(12) United States Patent
Alexandrov (10) Patent No.: US 6,893,993 B1
(45) Date of Patent: May 17, 2005

(54) POLYCRYSTALLINE MATERIAL, PROCESS FOR PRODUCING THEREOF, AND ARTICLES MANUFACTURED THEREFROM

(75) Inventor: Vladimir Iliich Alexandrov, Moscow (RU)

(73) Assignees: Vladimir Ivanovich Puzdaev, Vladivostok (RU); Vladimir Valentinovich Ermolin, Vladivostok (RU); Sergei Leonidovich Kochergin, Vladivostok (RU); Alexandr Semenovich Migunov-Nakhodka (RU)

( * ) Notice: Subject to any disclaimer, the term of this patent is extended or adjusted under 35 U.S.C. 154(b) by 246 days.

(21) Appl. No.: 10/149,359
(22) PCT Filed: Jun. 1, 2000
(86) PCT No.: PCT/RU00/00311
§ 371 (c)(1),
(2), (4) Date: Oct. 16, 2002
(87) PCT Pub. No.: WO01/44543
PCT Pub. Date: Jun. 21, 2001

(30) Foreign Application Priority Data

Dec. 15, 1999 (RU) .......................................... 99125820

(51) Int. Cl.⁷ ............................................ C04B 35/486
(52) U.S. Cl. ...................................... 501/103; 501/104
(58) Field of Search ................................. 501/103, 104

(56) References Cited

U.S. PATENT DOCUMENTS 4,153,469 A * 5/1979 Alexandrov et al. ........ 501/104
5,854,158 A * 12/1998 Nawa et al. ................ 501/104

FOREIGN PATENT DOCUMENTS

RU 2134314 * 8/1999

* cited by examiner

*Primary Examiner*—Karl Group
(74) *Attorney, Agent, or Firm*—Ladas & Parry (57) ABSTRACT

The proposed material consists of zirconium dioxide crystallites of tetragonal modification of acicular or platy form, having a size not exceeding 0.05 mm, oriented parallel to their long axes and forming a rectangular lattice. Such a structure of the material insures its increased resistance to the onset of cracking, this promoting high physico-mechanical characteristics of the material. The material is obtained under the conditions of lowered pressure by the method of melting in a cold container with its horizontal moving relative to an inductor. The physico-mechanical properties of the material make it possible to manufacture therefrom extremely sharp scalpels, which ensure the blade service life of up to 60 operations on dense tissues, the blades withstanding up to 10 resharpenings without changes in the blade profile.

12 Claims, 7 Drawing Sheets

POLYCRYSTALLINE MATERIAL, PROCESS FOR PRODUCING THEREOF, AND ARTICLES MANUFACTURED THEREFROM

1. FIELD OF THE ART

The invention relates to the field of new high-strength materials, namely to a single-phase polycrystalline material based on zirconium dioxide of tetragonal modification and to a process for producing thereof by high-frequency melting in a cold container.

Besides, the invention relates to processing and wear-resistant articles manufactured from a crystalline material and working under increased loads, and also to cutting tools used in medicine, which should have high strength, wear-resistance and longevity.

2. DESCRIPTION OF THE STATE OF THE ART

Materials based on zirconium dioxide have unique physical and mechanical characteristics: high hardness, wear-resistance, and at the same time an increased viscosity and plasticity. It is known that besides their chemical nature the characteristics of these materials are determined by their macro- and microstructure, which is formed both as a result of topochemical processes in starting materials (dehydration, recrystallization in a gradient temperature field, etc.) and depending on the process of preparing the material (sintering, pressing or melting) and also as a result of changes in the technological parameters of the employed process. For example, for obtaining materials comprising zirconium ceramics, methods of sintering and isostatic compression are used, and to obtain zirconium material having crystalline structure, different modifications of high-temperature melting are used.

The choice of the method of obtaining the material and the equipment depend on the characteristics of the starting compounds and the material to be obtained, and also on the requirements to the finished product, such as purity, defectiveness, structure, size, etc. As a rule, for a more economical use of the material, attempts are made to obtain material having a large size and suitable shape, because when dressing the crystalline material, cutting, grinding and polishing losses may amount to 80% of the starting material.

There is known a material based on zirconium (hafnium) dioxide stabilized with 10–30% of yttrium oxide (U.S. Pat. No. 4,153,469, publ. 08.05.79). The material comprises a single crystal of cubic modification of zirconium (hafnium) dioxide, and it is optically transparent. The monocrystalline structure of the material ensures its high microhardness (1300–1500 $kG/mm^2$), but involves a higher fragility and low viscosity and durability, this impeding extensive use of this material in industry.

The above-mentioned monocrystalline material is obtained by a method of direct high-frequency (HF) melting in a cold container. For this purpose, a starting charge consisting of zirconium or hafnium dioxide and stabilizing yttrium oxide in a preset ratio, is placed into a reaction container and melted by means of a high-frequency electric field. Then from the obtained colorless melt a single crystal is grown by raising the container with the melt from the melting zone with a speed of 2–30 mm per hour. As the container is being removed from the melting zone, single crystals begin to grow in the form of their conglomerate (block), which then easily can be divided into separate single crystals.

The method allows obtaining a material comprising cubic single crystals of stabilized zirconium or hafnium with a height of up to 8 cm and a cross-section of 0.5 to 4.0 $cm^2$.

To obtain a colored material a coloring oxide selected from the group of oxides of transition or rare-earth elements is added to the charge in an amount of up to 8 mol. %.

There is known a ceramic material containing (in mol. %): 96–98 of $ZrO_2$ and 2–4 of $Y_2O_3$ or 6–13 of $CeO_2$. The basis of the material (up to 90%) is constituted by zirconium dioxide of tetragonal modification (JP Application 62-30660, publ. 09.02.87). The material comprises sintered ceramics and consists of grains of irregular shape with a size not larger than 0.1 $\mu$m. This ceramics has high hardness, bending strength and viscosity, but because of the monoclinic phase of zirconium dioxide and the presence submicropores on the grain boundaries, the grains crumble out, whereby brittleness of the material increases and its wear resistance decreases.

To obtain ceramics, the powders of oxides constituting the ceramics are comminuted down to fine-dispersed particles of 0.1 $\mu$m in size, ground in water, polyvinyl styrene is added thereto, and the contents are mixed thoroughly to obtain slurry from which press-powder is produced by spray drying and then shaped under a pressure of 3 $ton/cm^2$. After burning-out the binder, the blank is sintered for an hour at 1480° C., then compacted by hot isostatic pressing at a temperature of 1400° C. and pressure of 1500 atm. (JP 62-30660, publ. 09.02.87).

The obtained ceramics has Vickers hardness of 1600 $kG/mm^2$ and bending strength of 600–900 MPa at 20° C. The above-described technology of producing ceramics does not make it possible to obtain material with a high density, and, consequently, with a sufficient mechanical strength of ceramic material. It is also a problem to obtain the starting powder with uniform granulometric composition throughout the volume and uniform distribution of the stabilizing oxide in zirconium dioxide. Besides, because of the tetragonal-monoclinic transformation during sintering and especially during isostatic compression, there originates a surface layer with a compression strain. This leads to the presence in the material of a monoclinic phase of zirconium dioxide in the material and to surface crumbling because of pulling out of ceramic grains when using the material whereby its wear resistance decreases.

It is known that zirconium dioxide single crystal of tetragonal modification, partially stabilized by 3.5 mol. % yttrium oxide has high hardness and viscosity (Martinez-Fernandez J., Jimenez Melendo M, Domingues-Rodriguez A., Heuer A. H. "Microindentation-induced transformation in 3.5 mol. %-yttria-partially-stabilized zirconia single crystal", J. Am. Ceram. Soc. 1991, p. 491). But the presented single crystals have a small size (10×5×3 mm). They are obtained by growing from melt in scull as inclusions in the cubic modification of zirconium dioxide and were used for studying the hardness of the zirconium dioxide single crystal of tetragonal modification in different directions.

There is known a material based on $ZrO_2$ partially stabilized by 2.5–3.5 mol. % yttrium oxide (RU Appl. 97112489, publ. 10.08.99). The material is obtained by melting in skull. A charge consisting of $ZrO_2$ and $Y_2O_3$ is loaded into a container with cooled walls and melted to form a melt in the skull. Subsequent directed crystallization of the melt is effected by moving the container a in vertical direction relative to an inductor, then, by lowering gradually the inductor power, the container is cooled first to 1200–1400° C., and then to room with the inductor switched off. Subsequent annealing of the obtained material is carried out in air at a temperature of 800–1400° C. for 1–10 hours or in a rarefied atmosphere under a pressure of $10^{-4}$ mm hg and at a temperature of 1100–2100° C. for 1–20 hours.

The known method leads to obtaining a material whose microstructure comprises randomly arranged domains having an irregular shape and a size of 100–200 nm (0.0001–0.0002 mm).

A decrease in the structure granularity brings about an increase in the wear resistance of the material. But such ultra-dispersed structure leads to the origination of a strained surface layer with an increased compression strain, this decreasing the resistance of the material to the cracking onset point and being a favorable factor in possible transformation of the tetragonal phase into the monoclinic one.

It is known that an increased tendency of the material to the development of surface cracks is testified by a higher breaking strength value, determined at room temperature by the chevron notch method in comparison with the same value determined by the ball indentation method (Fisher G., Zirconia: Ceramic engineering's toughness challenge., Am. Cer. Soc., Bull. 1986, 65, No. 10, 1355–1360), this being actually the case with the known material, for which the respective values are 17 MPa/m$^2$ and 11 MPa/m$^2$.

As a rule, high-temperature synthesis of materials based on stabilized zirconium dioxide is effected by melting in the HF field in a container with cooled walls, in which crystals are grown in a vertical direction.

However, when the crystalline substance grows in a vertical direction, thermal convection is difficult, this leading to a partial capture of melt and admixture drops which accumulate in intercrystallite grains and decrease the strength and wear resistance of the material. Besides, the vertical method of obtaining the material does not allow the obtaining of polycrystalline material having a sufficiently large size required in the industry.

Known in the art are products manufactured from a ceramic material, for instance, shaving blades, produced from a ceramic material containing no less than 90% of tetragonal zirconium dioxide and 2–4 mol. % of yttrium oxide (JP Appication 62-30660). However, the heterogeneous structure of the material containing an admixture of the monoclinic phase of zirconium dioxide, does not insure high wear resistance and strength of the blades.

Blades are known, produced from single crystal of diamond, sapphire or other substance similar to diamond (U.S. Pat. No. 5,317,938). But such blades are expensive, brittle, and can be produced only in a small size (not more than 10.0 mm).

Blades, produced from a material with domain structure are closest to the claimed ones (RU 97112489 publ. 10.08.99). But the structure of the material does not insure sufficient wear resistance of the blades.

3. DISCLOSURE OF THE INVENTION

The main object of the invention is to provide a polycrystalline material with such a microstructure that would make it possible to increase resistance of the material with respect to the onset of cracking and lead to an increase in the bending strength and wear resistance of the material, when using it In the manufacture cutting edges and high-strength articles.

The set object is accomplished by that the polycrystalline material, according to the invention, consists of crystallites of partially stabilized zirconium dioxide of acicular or platy tetragonal modification having a size not over 0.05 mm, ratio of the length to the maximum cross-section being at least 2:1, the crystallites being arranged parallel to their long axes and forming a rectangular lattice.

As the oxides stabilizing the tetragonal modification of zirconium dioxide, the material contains an oxide selected from the group of oxides of yttrium, cerium, magnesium, calcium.

It is expedient that the material should contain chromophoric ions, such as rare-earth cations and polyvalent cations of transition metals, selected from the series: cobalt, titanium, chromium, vanadium, manganese, iron, nickel, neodymium, lanthanum, praseodymium, cerium, samarium, europium, gadolinium, erbium, thulium, ytterbium and lutetium. These ions impart different color to the material. The amount of chromophoric additives in the material is not over 5 mol. %.

To impart black color to the material, it is expedient to treat it thermally at a temperature of 1650–1750° C. for at least 3 hours.

The set object is accomplished also by the proposed process of obtaining a material with the claimed structure, comprising the steps of loading a charge consisting of zirconium dioxide and a stabilizing oxide into a cooled container, melting the charge to form a melt, subsequent crystallizing a sample and cooling the container to a temperature of 1300–1400° C. by lowering inductor power, the melt being held for at least 3 hours before the commencement of crystallization, crystallization and cooling of the container to a temperature of 1300–1400° C. being carried out at a pressure lowered to 200–300 mm Hg, further cooling to room temperature being performed with the pressure being increased gradually for at least 24 hours, the entire process being effected by moving the container in a horizontal direction relative to the inductor.

After cooling the melt to 1300–1400° C., it is expedient to carry out remelting at a speed not higher than 100 mm/hr.

For preparing the charge, zirconium dioxide can be used in the form of a powder and in the form of crystals and wastes from the production of single crystals.

It is preferable as the stabilizing oxide to introduce into the charge a metal oxide, selected from the group of oxides of yttrium, cerium, magnesium, calcium.

To obtain a colored metal, it is preferable to introduce into the charge up to 5 mol. % of a coloring chromophoric cation of a metal selected from the group of transition or rare-earth elements (cobalt, titanium, chromium, vanadium, manganese, iron, nickel, neodymium, lanthanum, praseodymium, cerium, samarium, europium, gadolinium, erbium, thulium, ytterbium and lutetium).

As a rule, for producing the material, metal oxides containing not more than $10^{-2}$% of admixtures are used.

It is expedient to carry out subsequent annealing of the obtained material at a temperature of 600–1400° C. or at a temperature of 1100–2000° C. and a pressure lowered to $10^{-4}$–$10^{-1}$ mm Hg for 1–20 hours.

The set object is accomplished also by that the cutting blade is manufactured from a polycrystalline material, consisting of crystallites of partially stabilized zirconium dioxide of tetragonal modification having acicular or platy shape, a length not greater than 0.05 mm, a ratio of the length to the maximum cross-section of at least 2:1, the crystallites being arranged parallel to their long axes and forming a rectangular lattice.

5. EMBODIMENTS OF THE INVENTION

Figure 1:
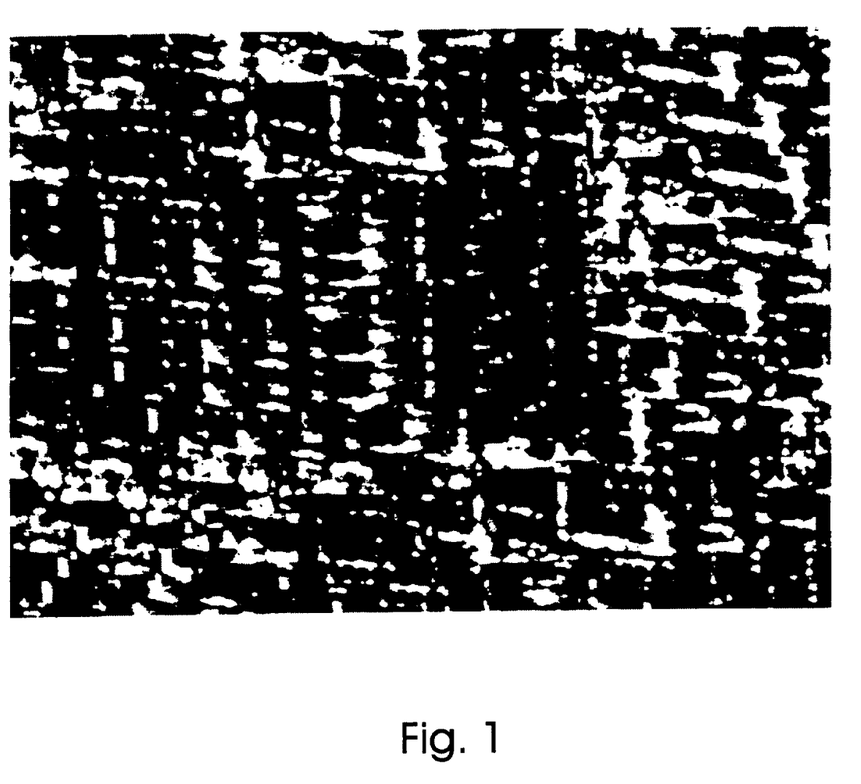
FIG. 1 shows a photograph of the structure of the claimed material, taken through a petrographic microscope at 1000× magnification.

A photograph of the structure of the claimed material, taken at 1000×magnification, is shown in FIG. 1.

According to x-ray phase analysis, the crystallites of which the material consists, are single crystals of partially stabilized zirconium dioxide of tetragonal modification, this being supported by the values of interplanar distances presented in the Table below, calculated from the data of x-ray phase analysis carried out on a diffractometer in Cu-radiation with a graphite monochromator. The sample is ground into powder and sown.

TABLE

| $a = b = 5.10$ A, $c = 5.16$ A, $V = 134.2$ | | | | |
|---|---|---|---|---|
| I/Io | d | h | k | I |
| 100 | 1.95 | 1 | 1 | 1 |
| 27 | 2.57 | 0 | 0 | 2 |
| 42 | 2.55 | 2 | 0 | 0 |
| 77 | 1.812 | 2 | 0 | 2 |
| 33 | 1.803 | 2 | 2 | 0 |
| 14 | 1.554 | 1 | 1 | 3 |
| 25 | 1.542 | 3 | 1 | 1 |
| 8 | 1.480 | 2 | 2 | 2 |
| 7 | 1.275 | 4 | 0 | 0 |
| 16 | 1.177 | 3 | 1 | 3 |

It is established that the structure of the claimed material is homogeneous, single-phase, without surface cracks. Numerous sections of the material, taken in all directions, give under microscope an image of a rectangular lattice, as in FIG. 1. Such structure of the material insures the origination of surface resistance to compression strain and causes resistance to the development and propagation of destructive cracks. Ultimately, this leads to an increase in the resistance of the material to the onset of cracking and increases its wear resistance. The above conclusion is supported by almost the same values of breaking strength, determined by the notch method (17 MPa/m$^2$) and by the ball indentation method (16 MPa/m$^2$).

It is established experimentally that if the size of the crystallites constituting the material is larger than the claimed one, it is impossible to achieve the necessary homogeneity of the composition and structure of the material because of the admixture of the monoclinic phase present therein and formation surface cracks of different directions, this, in its turn, leading to a decrease in wear resistance.

Color of the material depends on the presence therein of the chromophoric cation selected from the group of transition or rare-earth elements (cobalt, titanium, chromium, vanadium, manganese, iron, nickel, neodymium, lanthanum, praseodymium, cerium, samarium, europium, gadolinium, erbium, thulium, ytterbium and lutetium) in an amount of up to 5 mol. %. For example, the presence of 1.0 mol. % of nickel oxide provides greenish color, and 3.5 mol. % of erbium oxide colors the material pink.

Black color of the material, quite convenient when producing surgical blades, originates in subsequent annealing of the claimed material at a temperature of 1650–1750° C. for at least 3 hours.

Figure 2:
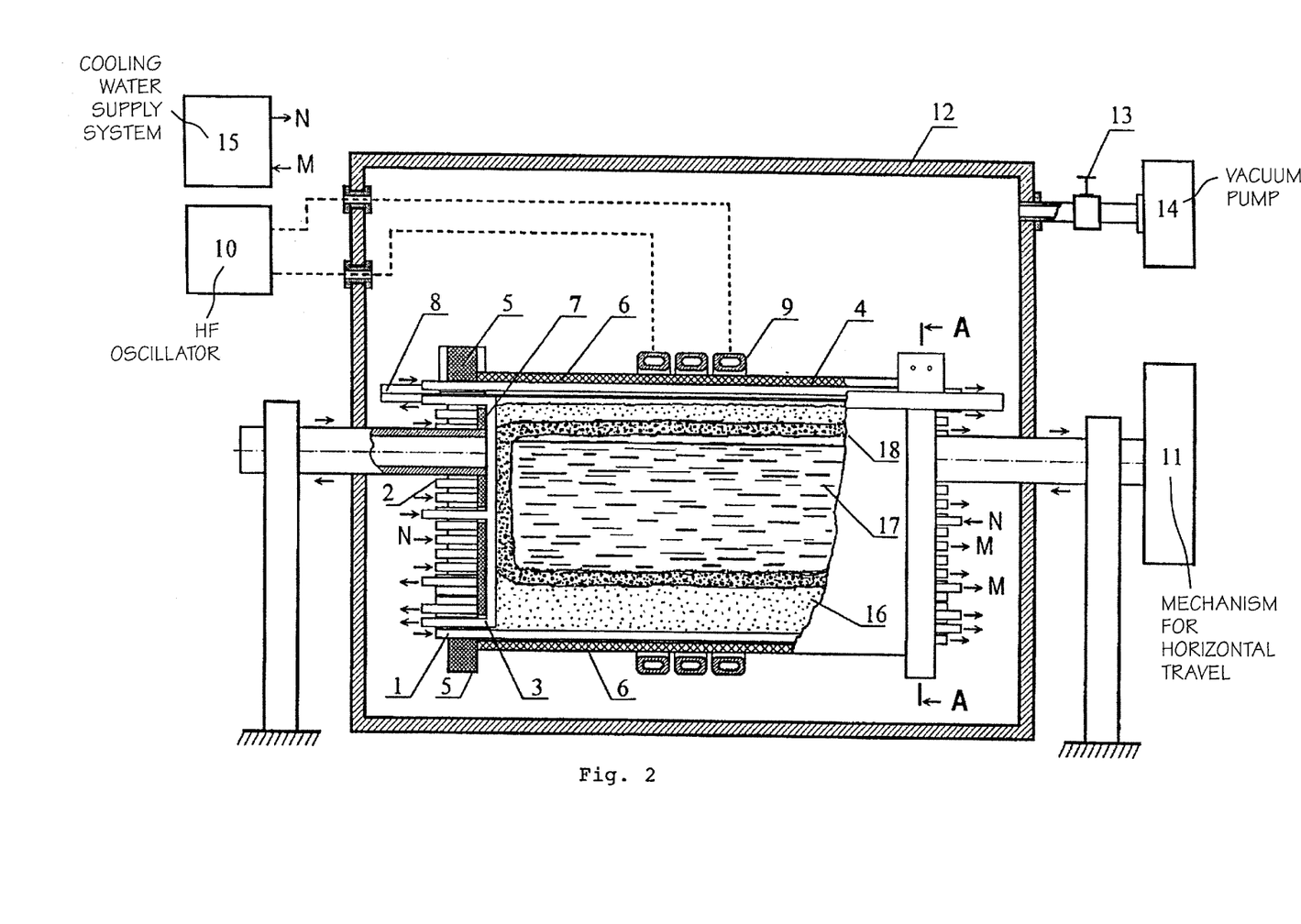
FIG. 2 shows a diagram of a device used for carrying out the process of producing polycrystalline material.
Figure 3:
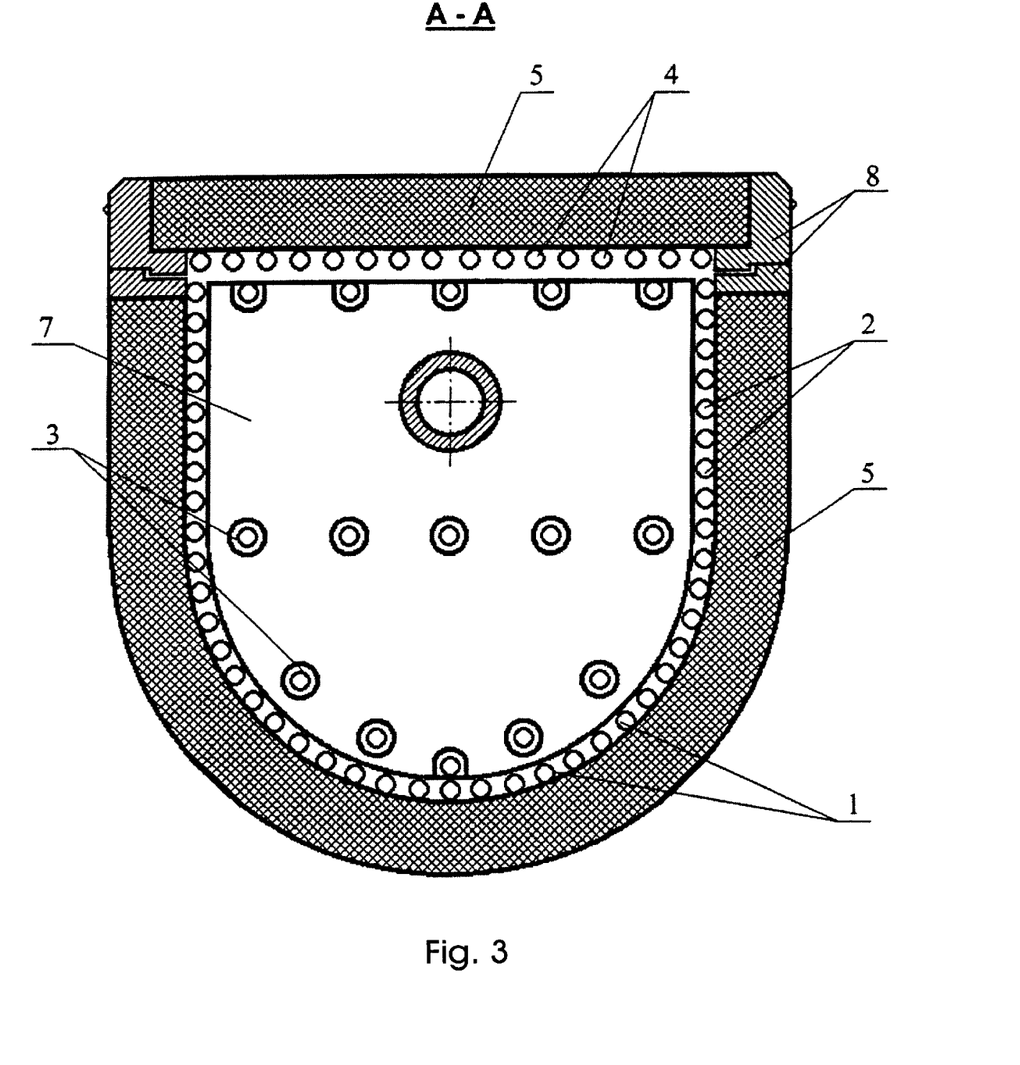
FIG. 3 shows a section taken along A—A of a container for producing the claimed material.

For carrying the process of obtaining the claimed material into effect, use is made of a device shown diagrammatically in FIG. 2 and FIG. 3. The device consists of a container constituted by a base 1 which is a semicylinder with vertical walls 2 having a height of 0.5–1 of the cylinder diameter, end walls 3, and a container cover 4. The container base 1 with the vertical walls 2, end walls 3 and cover 4 are assembled from a set of cooling tubes and/or sections secured on a nonconducting base 5. The container is placed within a quartz envelope 6, while the end walls are covered from the outside with a fluoroplastic plate 7. The base 1 and the cover 4 can move in guides 8 along the container base relative to each other. Around the quartz container envelope an inductor 9 of a high-frequency (HF) oscillator 10 is arranged. The container is connected to a mechanism 11 which provides for horizontal travel of the container relative to the inductor 9. The container and the inductor are placed into a hermetic case 12 which is connected through a regulating valve 13 to a vacuum pump 14. Cooling water is supplied to the tubes through a system 15 in a direction indicated by arrows N and withdrawn in a direction indicated by arrows M.

The device embodied so that the container is movable in a horizontal direction relative to the inductor and can be cooled from all sides, it is possible to grow polycrystalline material having the claimed structure and a volume of up to 1500 cm$^3$.

The process is carried out in the following way. A charge 16 consisting of ZrO$_2$, a stabilizing oxide, a metal entering into the stabilizing oxide, or metallic zirconium for promoting initial melting and an appropriate molar ratio of zirconium dioxide to the stabilizing oxide, is loaded to the base of the container. The charge is rammed and, if necessary, an additional amount of the charge is introduced to fill the container base completely. The container is closed with the cover 4 and the charge is melted in the HF field created with the help of the inductor 9 of the HF oscillator 10 with a frequency of 5.28 MHz and oscillating power of 60 kW. The charge is melted with the speed of the container travel relative to the inductor 9 not exceeding 100 mm/hr. The result is a melt 17 around which a skull 18 is formed. As a result of melting, gas and volatile compounds are removed completely from the melt, this providing additional purification from many admixtures that are volatile at the melting temperature (about 3000° C.) and are partially retained in intercrystallite pores when a conventional method (vertical travel of the container) is used. The melt is homogenized by holding it in molten state for at least 3 hours. Then in the case 12 a rarefaction to not over 200–300 mm Hg is created, and crystallization of the substance is started by moving the container in a reverse direction with a speed of 0.12–30 mm/hr. The speed of passing the melting zone should ensure homogeneity and single-phase state of the obtained material. As a rule, this speed is within the known range of 0.1–10 mm/hr. After that, external cooling being preserved, the power of the HF field is decreased, promoting lowering of the temperature with a speed not over 50° C. per hour down to 1300–1400° C., below which the energy of the HF field is not absorbed by the crystals. Further cooling to room temperature proceeds with gradual increase of pressure in the container up to the atmospheric one during at least 24 hours, whereafter the container is opened by shifting the cover 4 along the guides 8. A polycrystalline plate having a thickness of at least 50 mm and a surface amounting to 50–70% of the melt surface area in the container grows on the melt surface in the container base 1.

As the stabilizing oxide, an oxide selected from the group of oxides of yttrium, cerium, magnesium, calcium is added to the charge. The amount of the stabilizing oxide is determined by the necessity of obtaining stabilized tetragonal modification, and this amount is different, depending on the oxide. For example, for yttrium oxide the amount is 2–4 mol. %, for cerium oxide it is 6–13 mol. % and for magnesium oxide it is 4–8 mol. %.

Remelting of the material with a speed not over 100 mm/hr after cooling thereof to 1300–1400° C. increases the homogeneity of and orders the structure of the claimed material.

Adding up to 5 mol. % of a coloring chromophoric cation of a metal selected from the group of transition or rare-earth elements (cobalt, titanium, chromium, vanadium, manganese, iron, nickel, neodymium, lanthanum, praseodymium, cerium, samarium, europium, gadolinium, erbium, thulium, ytterbium and lutetium) makes it possible to obtain the claimed material with desirable color.

Subsequent annealing of the obtained material at a temperature of 600–1400° C. or at temperature of 1100–2000° C. and a pressure lowered to $10^{-4}$–$10^{-1}$ mm Hg for 1–20 hours leads to lowering of internal strains in the material, increasing its strength.

The claimed process ensures high homogeneity of the obtained material, stability of its phase composition and ensures the formation of the claimed structure of the material. Besides, the process ensures the claimed shape of a separate crystallite and an increase in the crystallite strength owing to a decrease in its defectiveness. This increases its cutting ability and makes it possible to produce extremely sharp, wear resistant articles.

It is established experimentally, that, when carrying out the process under conditions other than the claimed ones, it is impossible to achieve the claimed homogeneity and structure of the material, its single-phase state, and the absence of cracks.

The process is illustrated by the following Examples.

EXAMPLE 1

For carrying out the process, a device is used, which is shown diagrammatically in FIG. 1, FIG. 2 and FIG. 3. A charge consisting of 32.062 kg of $ZrO_2$ (97 mol. %) and 1.938 kg of $Y_2O_3$ (3 mol. %) is loaded into base 1 of a container having a length of 250 mm, a height of its vertical walls of 90 mm, and a diameter of its semicylinder of 150 mm. The loaded charge is thoroughly rammed. 30 g of metallic zirconium is added to the charge, and 2 g of $Y_2O_3$ is added to preserve the molar ratio. The container is closed with cover 4, HF oscillator 10 is switched on, initial melting is started, and then gradually all the charge is melted by moving the container in a horizontal direction relative to the inductor with a speed of 100 mm/hr. After the charge is melted, the melt is held for 8 hours. Then vacuum pump 14 is coupled via regulating valve 13, a rarefaction of 300 mm Hg is created, and the container is moved in a reverse direction with a speed of 1 mm/hr. Crystallization of the substance occurs. Then the inductor power is decreased, the container is cooled to 1300° C. with a speed of 50° C./hr. The HF oscillator 10 is switched off, and the pressure is increased gradually for 24 hours. Then the container is opened. A crystalline plate with a thickness of 55 mm and a surface area of 260 cm$^2$ (1430 cm$^3$) forms on the horizontal surface of the container base.

The plate comprises a polycrystalline material, consisting of tetragonal crystallites of zirconium dioxide. A section viewed through the microscope at ×1000 magnification confirms that the obtained material has a single-phase structure and is free of defects (FIG. 1). The breaking strength is 17 MPa/m$^2$ as determined by the method of chevron notch and 16 MPa/m$^2$ as determined by the ball indentation method.

EXAMPLE 2

Figure 4:
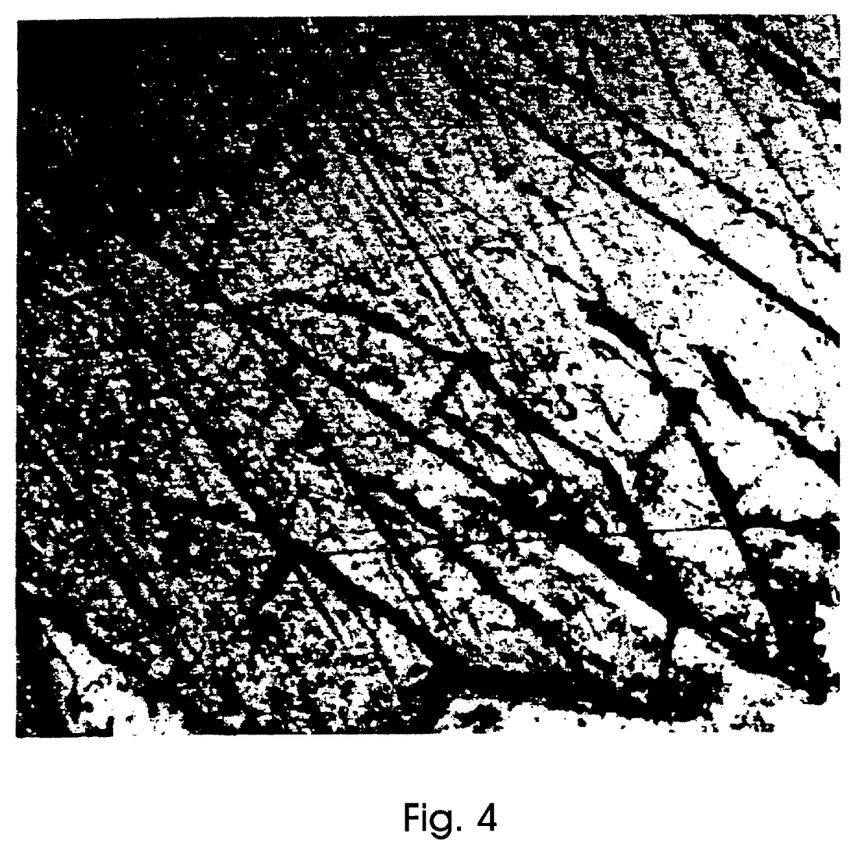
FIG. 4 shows a photograph of the material obtained under atmospheric pressure conditions, taken through a petrographic microscope.

A charge having a composition analogous to the composition of the charge, described in Example 1 is loaded into the container, and crystallization is carried out under conditions specified in Example 1, but under normal pressure. A material with a heterogeneous composition and surface cracks is obtained (FIG. 4).

It should be noted that any inobservance of the claimed conditions of obtaining material leads to disturbance of the material homogeneity and to the appearance surface cracks.

EXAMPLE 3

For the synthesis, a charge is used, consisting of 29.64 kg (96.5 mol. %) of $ZrO_2$ and 0.36 kg (3.5 mol. %) of MgO. To initiate melting, 30 g of metallic zirconium is introduced, and additionally 5 g of MgO to compensate for metal oxide formed during oxidation. Melting and crystallization are carried out as described in Example 1, with the exception that after cooling the melt to 1400° C. remelting and crystallization are carried out with a speed of 0.5 mm/hr.

A plate of partially stabilized polycrystalline single-phase zirconium dioxide is formed, having no defects, a breaking strength of 13 MPa/m$^2$ (as determined by the method of chevron notch) and of 12 MPa/m$^2$ (as determined by the method of ball indentation).

The plate thickness is 50 mm, surface area is 260 cm$^2$.

EXAMPLE 4

For the synthesis, a charge is used, consisting of 26.58 kg (90.0 mol. %) of $ZrO_2$ and 2.95 kg (10.0 mol. %) of $CeO_2$. To initiate melting, 30 g of metallic zirconium is introduced, and additionally 4.5 g of $CeO_2$ to compensate for metal oxide formed during oxidation. Melting and crystallization are carried out as described in Example 1, with the exception that the initially formed melt is kept for 5 hours before the commencement of crystallization, and, after cooling the melt to 1300° C., remelting is carried out with the speed of the inductor travel of 100 mm/hr., and crystallization is carried out with a speed of 2.5 mm/hr.

A 60 mm-thick plate of partially stabilized polycrystalline single-phase zirconium dioxide is formed, having a surface area of 255 mm$^2$, free of defects, having a breaking strength of 16 MPa/m$^2$ as determined by the method of chevron notch and of 15 MPa/m$^2$ as determined by the method of ball indentation, respectively.

EXAMPLE 5

For the synthesis, a charge is used, consisting of 29.6 kg (87.5 mol. %) of $ZrO_2$, 3.4 kg (10.0 mol. %) of $CeO_2$, and 0.85 kg (2.5 mol. %) of $Er_2O_3$. To initiate melting, 30 g of metallic zirconium is introduced, and additionally 4.5 g of $CeO_2$ to compensate for metal oxide formed during oxidation. Melting and crystallization are carried out as described in Example 1.

A 60 mm-thick plate of partially stabilized polycrystalline single-phase zirconium dioxide is formed, having no defects, a breaking strength of 16 $MPa/m^2$ as determined by the method of chevron notch and of 15 $MPa/m^2$ as determined by the method of ball indentation. The plate is pink-colored.

The physico-mechanical properties of the claimed material make it possible to produce therefrom cutting edges of different tools, for example, of medical scalpels of required size for carrying out surgical operations, and also articles operating under conditions of increased loads.

Blades manufactured from the claimed material have an increased wear resistance and working life of up to 60 operations on dense tissues, such as skin, apaneurosis, cicatricial tissue. An increased stability of the claimed material to the onset of cracking allows resharpening the cutting edge of blades up to 10 times without any changes of the blade profile.

Figure 5:
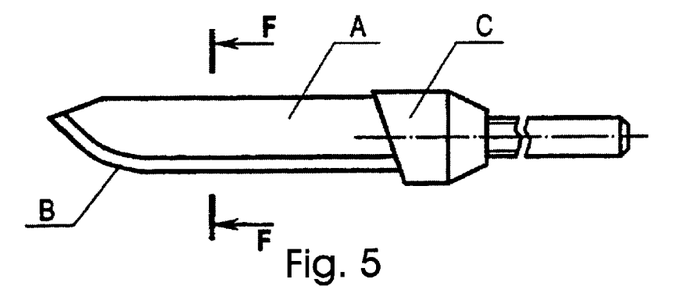
FIGS. 5–7 show samples of medical scalpels whose blades are manufactured from the claimed material.
Figure 6:
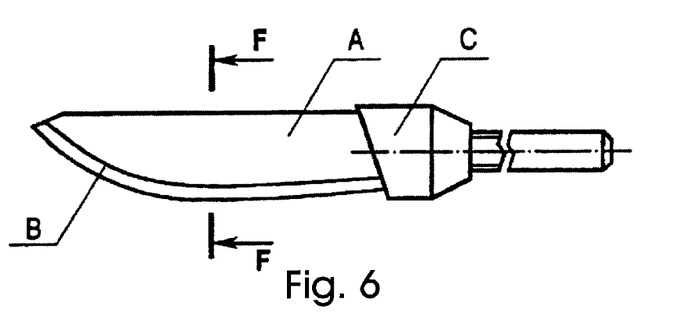
Figure 7:
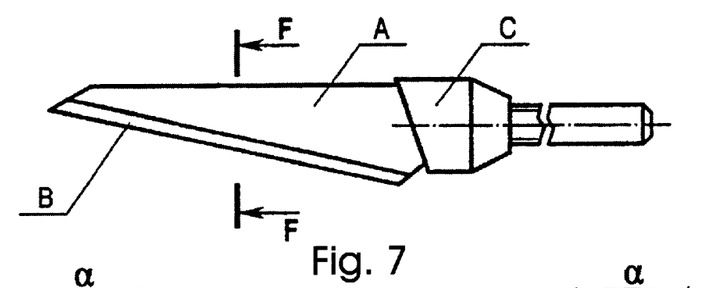
Figure 8:
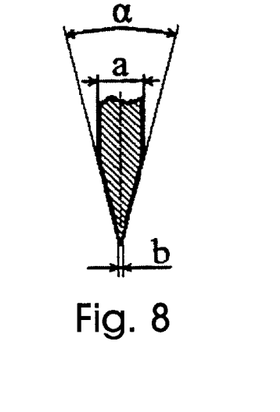
FIGS. 8, 9 show two types of blade sharpening.

FIGS. 4–6 show different types of medical scalpels whose blades are manufactured from the claimed material. FIGS. 7, 8 show two types of sharpening such blades.

To manufacture blades, the material is cut into 0.5–0.8 mm-thick plates with the help of a 0.2–0.3 mm-thick diamond cutting wheel. Then both sides of the plates are polished on both sides in several steps with diamond grinding wheels with abrasive grains of 20.0 μm in the initial step and of 1.0–2.0 μm in the final step. To obtain blade surfaces with a higher degree of finish, the wheels can be dressed with diamond pastes with an abrasive of 0.5–1.0 μm.

Then blanks for blades of different profiles are cut out from a polished plate of an arbitrary shape with the help of a laser apparatus and standard patterns. Next, an appropriate profile of the blade cutting edge, depending on the field of use (shaving, with a double angle of sharpening, with a slope on one side, etc.), is formed with a diamond sharpening tool. The final stage of sharpening the cutting edge of the blade is effected with a diamond sharpening tool with grains of 0.6 to 1.0 μm on precision sharpening equipment. Control of sharpness of the blade cutting edge by a radioelectron microscope showed that the diameter of the cutting edge rounding-off did not exceed 0.1 μm, and in some individual samples this value was 0.05 μm.

A scalpel shown in FIGS. 5–7 consists of blade A with cutting edge B and blade holder C. The blade A with the cutting edge B are manufactured from the claimed material. The blade holder C is made from steel. The blade A is attached to the holder C by gluing.

Figure 9:
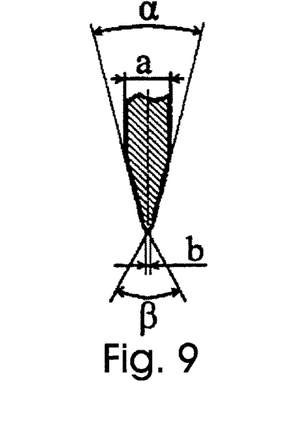
Figure 10:
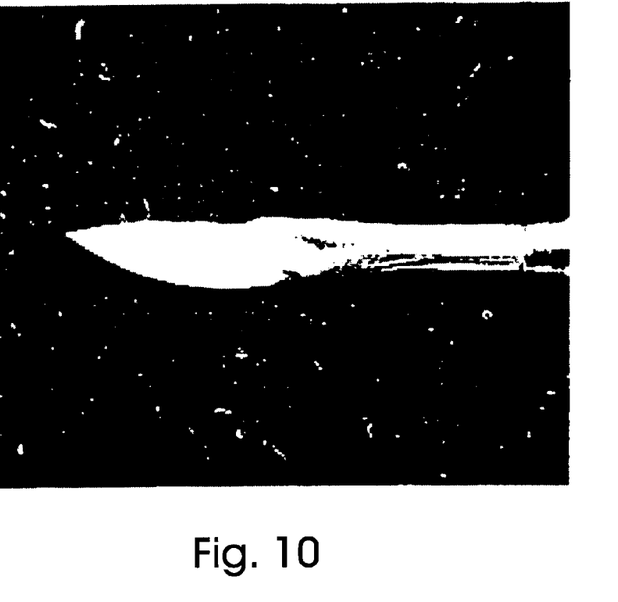
FIGS. 10–13 show photographs of products: medical scalpels of different profiles with blades from the claimed material.
Figure 11:
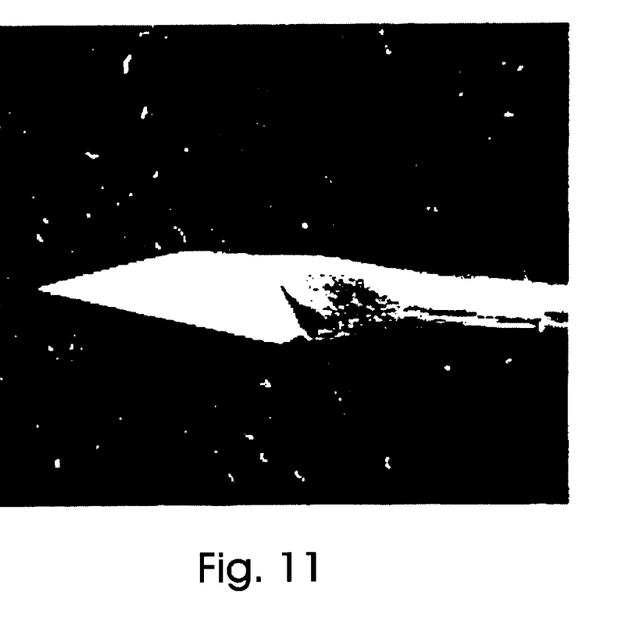
Figure 12:
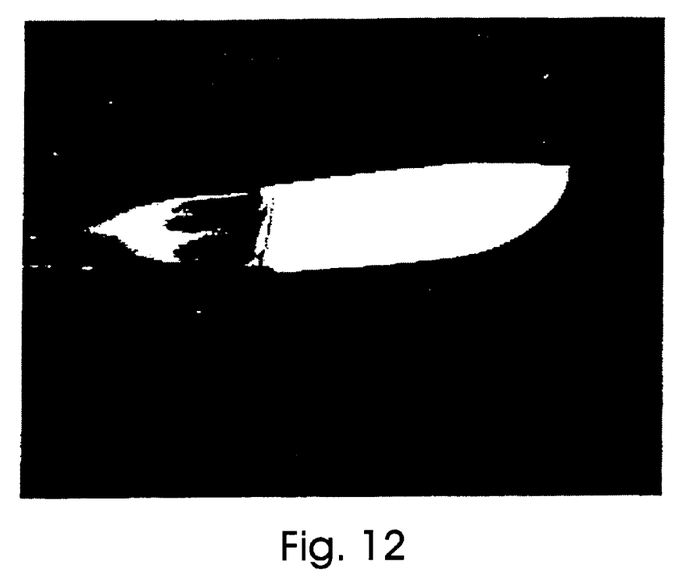
Figure 13:
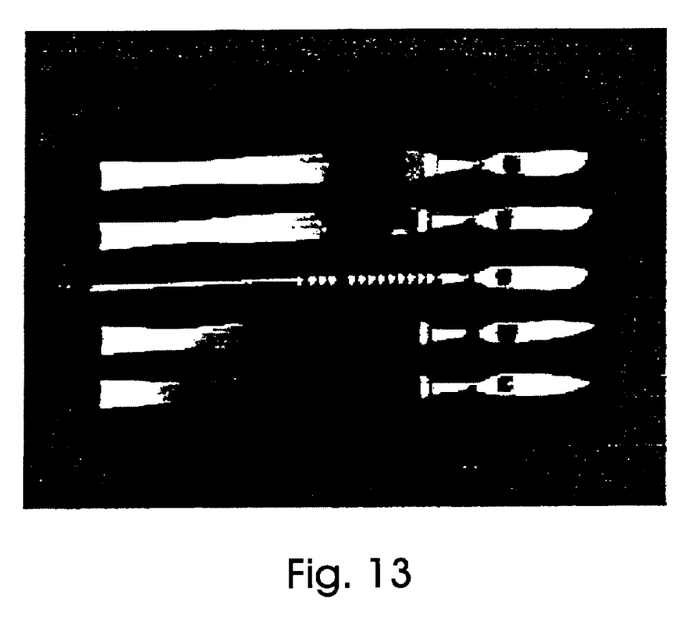

FIGS. 8, 9 illustrate two types of sharpening the blades, wherein a is the blade thickness equal to 0.4–0.5 mm; b is the diameter of rounding-off of the blade cutting edge, equal to 0.05–0.1 μm; α is the angle of sharpening equal to 25±1°; β is the angle of sharpening equal to 40±1°.

From the claimed material medical scalpels of different profiles were manufactured with blades whose photographs are shown in FIGS. 10–13.

Manufacturing blades from the claimed material makes it possible to prolong considerably the service life of the tools.

So, the use of the proposed technical solutions makes it possible, with the help of the claimed process, to obtain material based on tetragonal modification of partially stabilized zirconium dioxide, possessing an increased resistance to the onset of cracking, higher wear resistance and breaking strength, whereby increased longevity and wear resistance is imparted to articles manufactured from this material.

What is claimed is:

1. A polycrystalline material consisting of crystallites of partially stabilized zirconium dioxide, characterized in that the crystallites have acicular or platy shape, their length does not exceed 0.05 mm, the ratio of the length to the maximum cross-section is at least 2:1, the crystallites are arranged parallel to their long axes and form a rectangular lattice.

2. A polycrystalline material according to claim 1, wherein the zirconium dioxide contains a stabilizing oxide of a metal selected from the group consisting of yttrium, cerium, magnesium and calcium.

3. A material according to claim 1, characterized in that it further contains an oxide of a chromophore metal selected from the group of transition and/or rare-earth elements.

4. A material according to claim 3, characterized in that the amount of a chromophore metal oxide of is up to 5 mol. %.

5. A material according to claim 1, characterized in that it has black color obtained as a result of thermal treatment at a temperature of 1650–1750° C. for at least 3 hours.

6. A material according to claim 2, characterized in that it has black color obtained as a result of thermal treatment at a temperature of 1650–1750° C. for at least 3 hours.

7. A process of producing a polycrystalline material consisting of crystallites of partially stabilized zirconium dioxide, wherein the crystallites have acicular or platy shape, their length does not exceed 0.05 mm, the ratio of the length to the maximum cross-section is at least 2:1, the crystallites are arranged parallel to their long axes and form a rectangular lattice, the process comprising loading a charge consisting of zirconium dioxide and a stabilizing oxide into a cooled container, melting the charge to form a melt, subsequent crystallization by moving the container relative to an inductor with a speed of 0.1–30 mm/hr, cooling the container to a temperature of 1300–1400° C., characterized in that the process is carried out with the container being moved horizontally relative to the inductor, the melt is held for at least 3 hours before the onset of crystallization, the crystallization and cooling the container to temperature of 1300–1400° C. are effected at a pressure lowered to 200–300 mm Hg, and cooling to a temperature lower than 1400° C. is effected with a gradual increase of pressure for at least 24 hours.

8. A process according to claim 7, characterized in that zirconium dioxide is used in the form selected from the group comprising crystalline wastes, a powder, crystalline wastes and a powder.

9. A process according to claim 7, characterized in that an oxide of a metal selected from the group of oxides of yttrium, cerium, magnesium, calcium, is added to the charge as the stabilizing oxide.

10. A process according to claim 7, characterized in that after lowering the temperature of the container to 1300–1400° C. remelting is carried out with a speed of passage not over 100 mm/hr.

11. A process according to claim 7, characterized in that the formed material is subjected to annealing at a temperature of 600–1400° C. and atmospheric pressure or at a temperature of 1100–2000° C. and a pressure lower than $10^{-1}$ mm Hg for 1–20 hours.

12. A blade manufactured from the polycrystalline material according to claim 1.

* * * * *